United States Patent [19]

McEntire et al.

[11] Patent Number: 4,549,017

[45] Date of Patent: Oct. 22, 1985

[54] PROCESS FOR THE PRODUCTION OF N-SUBSTITUTED (METH)ACRYLAMIDES FROM (METH)ACRYLATES AND AMINES OVER A METAL OXIDE OR ALKOXIDE CATALYST

[75] Inventors: Edward E. McEntire; John F. Knifton; Edward C. Y. Nieh; Kathy B. Sellstrom, all of Austin, Tex.

[73] Assignee: Texaco Inc., White Plains, N.Y.

[21] Appl. No.: 535,010

[22] Filed: Sep. 23, 1983

[51] Int. Cl.[4] .................. C07D 295/10; C07C 102/06
[52] U.S. Cl. .................... 544/168; 564/135; 546/233; 548/579
[58] Field of Search ........ 564/135; 544/168; 546/233; 548/579; 252/194

[56] References Cited

U.S. PATENT DOCUMENTS

| | | | |
|---|---|---|---|
| 4,206,143 | 6/1980 | Wenzel et al. | 260/561 |
| 4,281,175 | 7/1981 | Kametani et al. | 560/217 |
| 4,301,297 | 11/1981 | Kametani et al. | 560/217 |
| 4,321,411 | 3/1982 | Nakamura et al. | 564/135 |
| 4,427,992 | 1/1984 | Ritchie et al. | 252/194 |

FOREIGN PATENT DOCUMENTS

| | | |
|---|---|---|
| 7834714 | 9/1976 | Japan . |
| 51-71010 | 12/1977 | Japan . |
| 52-153912 | 12/1977 | Japan . |
| 53-144522 | 12/1978 | Japan . |

OTHER PUBLICATIONS

Poller & Retout, "Organotin Compounds as Transestensification Catalysts", J. Organometallic Chemistry, 173 (1979), pp. C7–C8.

Primary Examiner—Charles F. Warren
Assistant Examiner—John A. Sopp
Attorney, Agent, or Firm—Jack H. Park; Kenneth R. Priem

[57] ABSTRACT

The invention is related to a catalytic method for the production of N-substituted (meth)acrylamides and is more particularly related to a catalytic method for the production of N-substituted (meth)acrylamides from (meth)acrylates and amines in the presence of an alkoxide of silicon, titanium or zirconium.

15 Claims, No Drawings

PROCESS FOR THE PRODUCTION OF N-SUBSTITUTED (METH)ACRYLAMIDES FROM (METH)ACRYLATES AND AMINES OVER A METAL OXIDE OR ALKOXIDE CATALYST

CROSS-REFERENCE TO RELATED PATENT APPLICATION

This application is related to U.S. application Ser. No. 382,858 filed May 28, 1982 and to U.S. patent application Ser. No. 469,860 filed Feb. 28, 1983 which are concerned, respectively, with the preparation of N-substituted (meth)acrylamides by the reaction of a (meth)acrylate ester and an amine over a catalytic amount of a dialkylmetal oxide catalyst such as a dialkylmetal dialkoxide catalyst, a dialkylmetal oxide catalyst or a metal alkoxide catalyst.

BACKGROUND OF THE INVENTION

1. Field of the Invention

The invention is related to a catalytic method for the production of N-substituted (meth)acrylamides and is more particularly related to a catalytic method for the production of N-substituted (meth)acrylamides from (meth)acrylates and amines in the presence of an alkoxide of silicon, titanium or zirconium.

2. Prior Art

U.S. Pat. No. 4,206,143 (corresponding to British patent application No. 2,021,101A) reveals that dialkyl stannic oxide catalysts, such as dibutyl stannic oxide, are effective for the preparation of N-substituted acrylamides and methacrylamides from the reaction of an alkyl ester of acrylic or methacrylic acid with an aliphatic, cycloaliphatic or aromatic amine, which is a primary or secondary amine.

U.S. Pat. No. 4,321,411, issued on Mar. 23, 1982, relates to a process for producing an N-substituted acrylamide or methacrylamide comprising reacting an acrylic or methacrylic acid ester with an aliphatic or aromatic amine in a liquid medium in the presence of a catalytic amount of an alkyltin alkoxide such as dibutyl dimethoxytin. This patent corresponds to British patent application No. 2,075,495A and Japanese Kokai No. 81-100,749.

Tin compounds are particularly useful as catalysts for the production of dialkylaminoethyl methacrylate. For example, Japanese Kokai No. 76-71,010 (CA 88:121898z) teaches that dialkyltin maleate, dialkyltin mercaptide and dialkylstannanediols are useful catalysts in this regard. Dibutyltin dimethoxide was found to be effective for the catalytic synthesis of dimethylaminoethyl methacrylate (DMAEMA), as described in Japanese Kokai No. 77-153,912 (CA 88:137169y). Further, compounds such as $(C_4H_9)_2Sn(O_2CR)_2$, where R is methyl or lauryl, are catalysts for the production of dialkylaminoethyl acrylates and methacrylates, as taught in Japanese Kokai No. 78-34,714 (CA 89:44410a).

U.S. Pat. No. 4,301,297 reveals that DMAEMA may be prepared in high yield by subjecting methyl methacrylate and dimethylaminoethanol to transesterification in the presence of di-n-octyl tin oxide as a catalyst. Compounds such as $(C_4H_9)_2SnR_2$ (where $R_2$ is hydrogen or $-OCH_3$ or $O_2CCH=CHCO_2$), $(n-C_8H_{17})_2\text{-}SnO$, $(C_6H_5)_3SnOCH_3$ or $(C_4H_9)_3SnO_2CCH=CH\text{-}C-O_2Sn(C_4H_9)_3$ are effective in the manufacture of dialkylaminoethyl acrylates as seen in Japanese Kokai No. 78-144,522 (CA 90:169290p). In addition, U.S. Pat. No. 4,281,175 discloses that DMAEMA may be made via a number of tin catalysts such as tetrabutyltin, trioctyltin ethoxide, dibutyltin dimethoxide, dibutyltin dihydride, dibutyltin dilaurate, dibutyltin maleate, bis(tributyltin)oxide and bis(dibutylmethoxytin)oxide. See also Poller, R. C., et at., "Organotin Compounds as Transesterification Catalysts", *Journal of Organometallic Chemistry*, 173(1979) pp. C7–C8.

The above mentioned related patent applications cross-referenced at the beginning of this specification are also relevant in respect of the prior art.

SUMMARY OF THE INVENTION

This invention concerns an improvement in a process for the preparation of N-substituted acrylamides. In accordance with the present invention the reaction is conducted after an alkoxide of silicone, titanium, or zirconium has been added to the feed in order to substantially remove water and to thereby substantially reduce the amount of by-product formed by the Michael reaction.

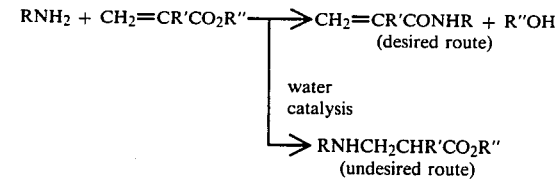

The basic process is directed to the preparation of N-substituted acrylamides of the formula:

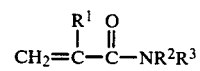

where $R^1$ is hydrogen or methyl, $R^2$ is hydrogen or lower alkyl of 1 to 4 carbon atoms, and $R^3$ is alkyl, aryl, alkaryl, aralkyl or alkoxyalkyl of one to twenty carbon atoms or

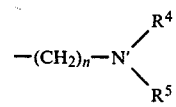

where n is an integer from 2 to 6 and $R^4$ and $R^5$ taken singly are lower alkyl groups of 1 to 4 carbon atoms, or $R^4$ and $R^5$ taken jointly are combined with the N' atom to form a heterocyclic ring group selected from the group consisting of morpholine, pyrrolidine or piperline ring groups, which process comprises reacting an acrylate ester of the formula:

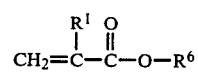

where $R^1$ is defined as above and $R^6$ is a lower alkyl of 1 to 4 carbon atoms with an amine of the formula $HNR^2R^3$ where $R^2$ and $R^3$ are defined as above over a catalytic amount of an alkyl metal oxide, an alkyl metal alkoxide, or a metal alkoxide catalyst having the formulae:

$$(R^7)_yM(OR^7)_x \text{ or } (R^7)_yMO$$
$$\text{(I)} \qquad \text{(II)}$$

where M is a metal atom selected from the group consisting of lanthanum, niobium, tantalum, copper, zinc, tin, lead, antimony and bismuth, $R^7$ is a lower alkyl group of one to four carbon atoms and x and y are each 0 to 5 and the sum of x+y is two to five depending on the valence of the metal atom for formula I; and wherein y is 1 to 3, depending on the valence of the metal, for formula II.

The catalysts useful in the method of this invention are metal alkoxides or alkylmetal oxides. The metal must have a valence of two to five. Examples of the metal oxides and metal alkoxides which may be suitable in the process of this invention may be represented by the formulae:

$$(R^7)_yM(OR^7)_x \text{ or } (R^7)_yMO$$
$$\text{(I)} \qquad \text{(II)}$$

where M is a metal atom selected from the group consisting of lanthanum, niobium, tantalum, copper, zinc, tin, lead, antimony and bismuth, $R^7$ is a lower alkyl group of one to four carbon atoms, x and y are each 0 to 5 and the sum of x+y is two to five depending on the valence of the metal atom and the sum of x+y is 2 to 5, equal to the valence of the metal or, in formula II, $R^7$ is lower alkyl and y is 1 to 3, depending on the valence of the metal. In addition to the metals noted above, metals in the same Periodic Table Groups may be expected to form active metal alkoxide compounds. The elements would be those metals of Group IIIB, VB, IB, IIB, IVA and VA such as vanadium, silver, cadmium, germanium and the like.

The alkoxy groups contain alkyl substituents having one to four carbon atoms and can either be straight or branched.

The desired N-substituted acrylamides have the formula:

$$\underset{\underset{\text{CH}_2=\text{C}-\text{C}-\text{NR}^2\text{R}^3}{|\phantom{xx}\|}}{\phantom{x}R^1\phantom{xx}O\phantom{x}}$$

where $R^1$ is hydrogen or methyl, $R^2$ is hydrogen or lower alkyl of one to four carbon atoms and $R^3$ is alkyl, aryl, alkaryl, aralkyl or alkoxyalkyl, each of which may have one to twenty carbon atoms. The $R^3$ group may also be:

$$-(CH_2)_n-N\begin{matrix}\nearrow R^4\\ \searrow R^5\end{matrix}$$

where n is an integer of from 2 to 6 and $R^4$ and $R^5$ when taken singly are lower alkyl groups containing 1 to 4 carbon atoms, or $R^4$ and $R^5$ when taken jointly are combined with the N' atom to form a heterocyclic ring group selected from the group consisting of morpholine, pyrrolidine or piperidine ring groups. These acrylamides are formed from two reactants, an acrylate ester and an amine. A common and preferred acrylamide is dimethylaminopropylmethacrylamide (DMAPMA) which is made from methyl methacrylate (MMA) and dimethylaminopropylamine (DMAPA).

The acrylate ester has the formula:

$$\underset{\underset{\text{CH}_2=\text{C}-\text{C}-\text{O}-\text{R}^6}{|\phantom{xx}\|}}{\phantom{x}R^1\phantom{xx}O\phantom{x}}$$

where $R^1$ is defined as above and $R^6$ is a lower alkyl of one to 4 carbon atoms.

The preferred acrylates or methacrylates are methyl acrylate, ethyl acrylate, methyl methacrylate and ethyl methacrylate since these are readily accessible industrially and the alcohol liberated upon aminolysis can easily be removed from the reaction mixture. As the number of carbon atoms in the alcohol radicals increases, the suitability of the esters decreases. For that reason, the alkyl esters having more than 4 carbon atoms in the alkyl radical are considered as less preferred. Methyl acrylate and methyl methacrylate are especially preferred.

The amines useful in this invention are primary and secondary amines containing various substituents. These amines may be represented by the formula $HNR^2R^3$ where $R^2$ and $R^3$ are defined as above. These substituents may be alkyl, aryl, alkaryl, aralkyl, dimethylaminoalkyl, diethylaminoalkyl, isopropylaminoalkyl, t-butylaminoalkyl, alkoxyalkyl and the like. This is a partial list and is not intended to limit the above definition. Examples of specific amines which would be suitable are butylamine, 2-octylamine, benzylamine, dimethylaminoneopentanamine, 3-dimethyl-aminopropylamine, 2-dibutylaminoethylamine, 4-(aminopropyl)morpholine, 3-diethylaminopropylamine, 2-dimethylaminoethylamine, 1-(aminopropyl)piperidine, 4-(aminoethyl)morpholine and similar compounds. A preferred compound is 3-dimethylaminopropylamine.

The reaction should be conducted at a temperature in the range of about 70° to 130° C. The preferable temperature range is 90° to 120° C. Reaction pressure should be approximately atmospheric. Reduced pressures are used as required to keep the temperature within the desired range to avoid polymerization. Increased pressure may be used with low boiling reagents. The mole ratio of amine to acrylate ester should range from about 1:1 to 1:100. The amine may be added gradually during the reaction to maintain a desired mole ratio of amine to ester. The mole ratio of amine to catalyst should range from about 1:0.8 to about 1:0.001. As will be demonstrated, the alcohol by-product need not be removed during the reaction which would permit continuous processing, a feature not seen in many previous methods. Batch processing could, of course, be used in connection with the inventive method. The use of inhibitors to prevent the polymerization of the desired acrylamide product may also be desired. Such inhibitors include phenothiazine, N,N'-diphenylphenylenediamine, p-methoxyphenol, etc.

It has been discovered in accordance with the present invention that the alkoxides of silicon, titanium, or zirconium are very effective drying agents for amines such as DMAPA, as well as for esters such as methylmethacrylate. In accordance with the present invention the alkoxide drying agent is added in approximately stoichiometric amounts according to the water present in the reagent to be dried. We have discovered that the drying is very rapid, that no solid residue is obtained, and that the reagents may be used directly for (meth)acrylamide formation. By removing water, the drying agents significantly improve the selectivity of this reaction because of the suppression of the Michael reaction which requires the presence of water as a coreactant. However, the drying agents do not substantially adversely affect the selectivity of the (meth)acrylamide formation reaction.

The alkoxide group of the drying agent of the present invention may suitably be methoxide, ethoxide, propoxide, isopropoxide, n-butoxide, sec-butoxide, isobutoxide, etc.

The alkoxide drying agents of the present invention are preferably added to the reactants prior to their introduction into the reactor. Once mixed, the alkoxide agents rapidly dry the feedstock without agitation. The alkoxide drying agent of the present invention may be added after the amine and the ester have been mixed. It is desirable, although not essential, to add the alkoxide drying agents to remove water prior to the introduction of the catalyst, since some catalysts are destroyed by water. The drying agents of this invention are effective at ambient temperatures but may also be used at elevated temperatures. The rate of drying may be improved by heating.

The alkoxide drying agents of the present invention react with water by hydrolysis. They are thus destroyed by the reaction of water and release alcohols into the solution. These alcohols may be removed by distillation during the subsequent stages of the process.

SPECIFIC EXAMPLES

Example I

To a one-liter glass reactor equipped with a 2-ft, 1-in. diameter column and a thermometer and addition funnel were charged:
400 g methyl methacrylate (MMA)
1.2 g N,N'-diphenyl-p-phenylenediamine (DPPDA)
1.2 g phenothiazine
8.4 g tetramethyl orthosilicate drying agent
5.0 g stannous methoxide catalyst The addition funnel was charged with 136 g (3-dimethylamino)propylamine (DMAPA).

The contents of the reactor were heated under a nitrogen atmosphere to 98° C. and the dropwise addition of DMAPA was begun. The methanol-MMA azeotrope was removed by distillation as it was formed during the reaction. The DMAPA was added over 1.5 hours. After 5.5 hours, the heat was removed. A total of 51 cc of overhead had collected.

Gas chromatographic analysis showed that the solution contained 42% of the desired N-(3-dimethylaminopropyl)methacrylamide (DMAPMA) and only 4.9% of the undesired Michael adduct [methyl (3(3-dimethylaminopropyl amino)-2-methyl) propionate]. The other major components were identified as 48.3% MMA and 1.9% DMAPA.

Example II

Dry bottles sealed with rubber serum stoppers were filled with 100 ml of DMAPA. A nitrogen atmosphere was provided for each bottle. Drying agents were added to the DMAPA in the bottles which were then shaken to mix the contents. The bottles then remained at room temperature until the analysis of the DMAPA in each for water by a modified Karl Fisher titration. The results are presented below:

TABLE 1

| Experiment | Water Content[1] of DMAPA Before Drying (ppm) | Amount of Drying Agent Added (g) | Time Until Analysis (hr) | Water Content[1] of DMAPA After Drying (ppm) |
|---|---|---|---|---|
| 5710-13-5 | 565 | $Si(OCH_2CH_3)_4$ (0.62) | 5.85 | 98 |
| 5710-13-6 | 565 | $Zr(O(CH_2)_3CH_3)_4$ (0.86) | 6.10 | 176 |
| 5710-13-3 | 565 | $Ti(O(CH_2)_3)_4$ (0.83) | 5.50 | 362 |
| 5710-13-1 | 565 | $B(OCH_3)_3$ (0.29) | 5.25 | 618[3] |
| 5642-91-5 | 1800[2] | $B(OCH_2CH_2OCH_3)_3$ (2.25) | 1.0 | 1776 |
| 5642-91-1 | 1800[2] | $Si(OCH_3)_4$ (0.38) | 1.0 | 257[2] |

[1]Average of two analyses; maximum deviation ±15 ppm. unless noted.
[2]±200 ppm.
[3]Excess water observed is believed to have been introduced by the $B(OCH_3)_3$.

These experiments illustrate the rapid drying activity of the alkoxides of silicon, zirconium, and titanium while showing the inactivity of boron alkoxides as drying agents under these conditions.

Example III

To apparatus similar to that of Example I were charged:
400 g MMA (water content 0.08%)
1.2 g DPPDA
1.2 g phenothiazine
5.0 g stannous methoxide catalyst
No drying agent was added.

The addition funnel was charged with 136 g DMAPA (water content 0.12%). The experiment was conducted exactly as Example I. Less overhead collected, however, and the experiment was terminated after 4 hours due to the slow nature of the reaction.

Gas chromatographic analysis showed that the resulting solution contained only 10.2% of the desired DMAPMA, and 14.1% of the undesired Michael adduct. The other components identified were 60.2% MMA and 14% DMAPA. Thus the water present in the feeds deactivated some of the catalyst causing the slower reaction in comparison to Example I.

Example IV

To an apparatus similar to that of Example I were charged:
405g MMA*
1.2 g DPPDA 1.2 g phenothiazine
6.43 g dibutyltin oxide catalyst To the addition funnel was charged 137 g DMAPA** containing 2.7 g of tetramethyl orthosilicate during agent. The DMAPA was added slowly as in Example I. At the end of 6.25 hours reaction time and a maximum reaction temperature of 121° C., the reactor contents were analyzed by gas chromatography. The product DMAPMA accounted for 50.1% whereas the Michael adduct was only 5.0% of the mixture. Other products identified were MMA (40.0%) and DMAPA (0.2%). Thus the conversion was 99.2%, and the selectivity to product was 87.7%.

*The MMA contained 774 ppm water. Before the MMA was introduced into the reactor, 2.4 g of tetraethyl orthosilicate (slightly less than one mole of drying agent per mole of water present in the MMA) was added to the MMA.
**The DMAPA contained 3472 ppm water before the addition of the drying agent. Thus one mole of tetraethyl orthosilicate was added for every 2 moles of water present.

Example V

In an experiment conducted similarly to Example IV, but using no added liquid drying agent, only 84% selectivity to DMAPMA was observed at 99% DMAPA conversion. The DMAPA and MMA were predried with molecular sieves to 587 ppm and 126 ppm water, respectively.

Example VI

In an experiment conducted similarly to Example IV where tetrabutyltitanate was used as a drying agent instead of tetraethyl orthosilicate, 88% selectivity to DMAPMA was observed at 99% DMAPMA conversion. The MMA containing 1424 ppm water was predried with 3.0 g tetrabutyl titanate. The DMAPA containing 2577 ppm water was dried with 3.0 g tetrabutyl titanate.

These examples illustrate the efficiency of these drying agents in the selective formation of the desired monomer. Even trace amounts of water remaining (Example V) in the reactor feeds can significantly influence the selectivity of the reaction.

The foregoing examples are given by way of illustration and not as limitations on the scope of this invention, which is defined solely by the claims appended hereto.

What is claimed:

1. In a process for the preparation of N-substituted acrylamides of the formula:

$$CH_2=C(R^1)-C(=O)-NR^2R^3$$

where $R^1$ is hydrogen or methyl, $R^2$ is hydrogen or lower alkyl of 1 to 4 carbon atoms and $R^3$ is alkyl, aryl, alkaryl, aralkyl or alkoxyalkyl containing 1 to 20 carbon atoms or $$-(CH_2)_n-N(R^4)(R^5)$$

where n is an integer from 2 to 6 and $R^4$ and $R^5$ taken singly are lower alkyl groups containing 1 to 4 carbon atoms or $R^4$ and $R^5$ taken jointly are combined with the N' atom to form a heterocyclic ring group selected from the group consisting of morpholine, pyrrolidine or piperidine ring groups, which process comprises reacting a water-containing acrylate ester feedstock of the formula:

$$CH_2=C(R^1)-C(=O)-O-R^6$$

where $R^1$ is defined as above and $R^6$ is lower alkyl of 1 to 4 carbon atoms with a water-containing amine feedstock of the formula $HNR^2R^3$ where $R^2$ and $R^3$ are defined as above over a catalytic amount of a metal alkoxide catalyst having the formula:

$$(R^7)_y M(OR^7)_x \quad \text{or} \quad (R^7)_y MO$$
$$(I) \qquad\qquad (II)$$

where M is a metal atom selected from the group consisting of lanthanum, niobium, tantalum, copper, zinc, tin, lead, antimony and bismuth, $R^7$ is a lower alkyl group of one to four carbon atoms, in formula I x and y are each zero through five and the sum of x+y is 2 to 5, depending on the valence of the metal, and in formula II y is 1 to 3 depending on the value of the metal, the improvement which comprises pretreating said feedstocks with a $C_1$–$C_4$ tetralkoxide of silicon, titanium or zirconium prior to said reaction, the amount of said tetralkoxide used being at least stoichiometrically equivalent to the amount of water in said feedstocks.

2. A method as in claim 1 wherein the amount of tetralkoxide that is used is essentially stoichiometrically equivalent to the amount of water present in said feedstocks.

3. A method as in claim 2 wherein the tetralkoxide is a silicon tetraoxide.

4. A method as in claim 3 wherein the silicon tetraoxide is tetraethylorthosilicate.

5. A method as in claim 2 wherein the tetralkoxide is a zirconium tetroxide.

6. A method as in claim 5 wherein the zirconium alkoxide is tetrabutyl orthozirconate.

7. A method as in claim 2 wherein the tetralkoxide is a titanium alkoxide.

8. A method as in claim 7 wherein the titanium tetralkoxide is tetrabutylorthotitanate.

9. In a process for the preparation of dimethylaminopropylmethacrylamide which comprises reacting water-containing methyl methacrylate with water-containing dimethylaminopropylamine in the presence of a polymerization inhibitor and a catalytic amount of a tin alkoxide or an alkyl tin oxide catalyst, the improvement which consists of pretreating said feedstocks prior to said reaction with an amount of a $C_1$–$C_4$ tetralkoxide of silicon, titanium or zirconium which is at least stoichiometrically equivalent to the amount of water in said feedstocks.

10. A method as in claim 9 wherein the tetralkoxide is a silicon tetraoxide.

11. A method as in claim 10 wherein the silicon tetraoxide is tetraethylorthosilicate.

12. A method as in claim 9 wherein the tetralkoxide is a zirconium tetroxide.

13. A method as in claim 12 wherein the zirconium tetroxide is tetrabutyl orthozirconate.

14. A method as in claim 9 wherein the tetralkoxide is a titanium alkoxide.

15. A method as in claim 14 wherein the titanium tetralkoxide is tetrabutylorthotitanate.

* * * * *